United States Patent [19]

Walker

[11] Patent Number: 4,618,586
[45] Date of Patent: Oct. 21, 1986

[54] APPARATUS FOR ADMINISTERING A CONTROLLED DOSAGE OF A CHEMICAL SUBSTANCE HAVING AN IMPROVED CULTURE CHAMBER

[75] Inventor: Robert D. Walker, Ham Lake, Minn.

[73] Assignee: Endotronics, Inc., Minneapolis, Minn.

[21] Appl. No.: 483,284

[22] Filed: Apr. 8, 1983

[51] Int. Cl.[4] .................. A01N 1/02; C12M 1/36; C12M 3/00

[52] U.S. Cl. .................................. 435/1; 435/289; 435/283; 435/284

[58] Field of Search ............... 222/52, 56; 364/413, 364/414, 415, 416; 604/50, 66; 435/1, 2, 89, 291, 283, 284, 813, 287, 296

[56] References Cited

U.S. PATENT DOCUMENTS

| | | | |
|---|---|---|---|
| 3,275,528 | 9/1966 | Ainis | 435/284 X |
| 3,531,258 | 9/1970 | Merrifield et al. | 422/116 |
| 3,557,077 | 1/1971 | Brunfeldt et al. | 260/112.5 R |
| 3,647,390 | 3/1972 | Kubodern et al. | 422/116 X |
| 3,926,737 | 12/1975 | Wilson et al. | 435/289 X |
| 4,395,492 | 7/1983 | Rees | 435/283 |

Primary Examiner—Robert J. Warden
Assistant Examiner—Randall E. Deck
Attorney, Agent, or Firm—Kinney & Lange

[57] ABSTRACT

An apparatus delivers a dosage of a chemical stimuli or drug in such a controlled manner that the concentration at the point of delivery is known at each and every point in time. The apparatus includes a plurality of vessels with each vessel containing a different concentration of the drug or chemical stimuli. A valve has a plurality of inlets and a single outlet wherein each inlet is connected to a corresponding vessel. An improved culture chamber is fluidly connected to the outlet of the valve and is used to develop the desired concentration. A first pump is positioned preferably between the valve and the chamber to provide a transport force for delivering the chemical stimuli or drug to the chamber. A suction tube is positioned proximate the top of the chamber and has a bottom open end which defines the level of liquid within the chamber. The suction tube thereby keeps the volume within the chamber constant. A second pump provides a transport force for removing excess liquid from the chamber. The valve, the first pump and the second pump are controlled by a computer control system. The computer control system determines which inlet of the valve is fluidly connected to the outlet to provide a preselected concentration of the chemical substance to the chamber with the pump being controlled by the computer to provide a predetermined flow rate of the medium to the chamber. The second pump is controlled by the computer removing excess volume from the chamber to insure that the volume within the chamber is kept constant. The control of the valve, the first and second pumps, are such that the concentration of the chemical stimuli or drug in the chamber is controlled and known at each and every point in time.

7 Claims, 8 Drawing Figures

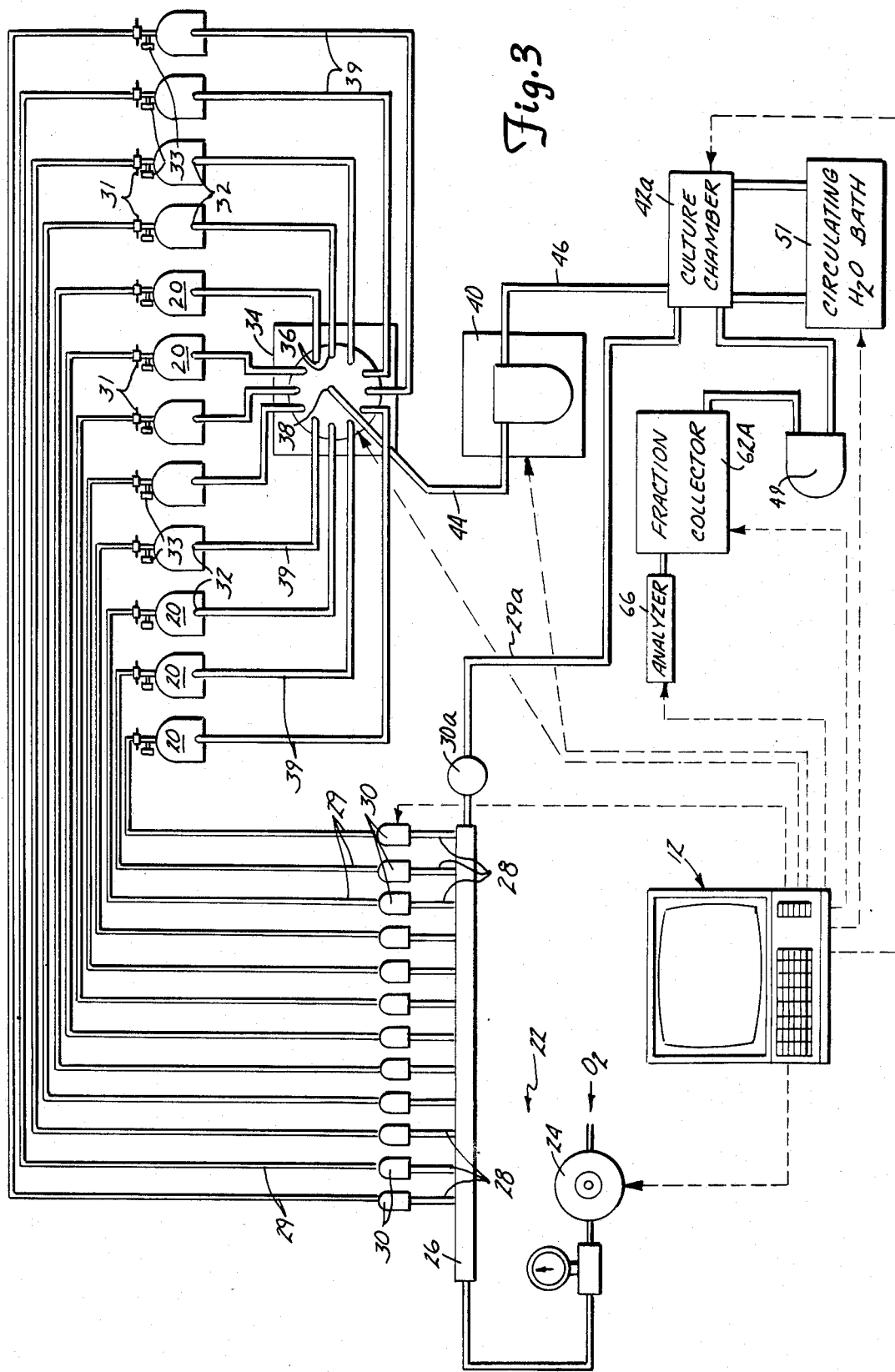

APPARATUS FOR ADMINISTERING A CONTROLLED DOSAGE OF A CHEMICAL SUBSTANCE HAVING AN IMPROVED CULTURE CHAMBER

BACKGROUND OF THE INVENTION

1. Field of the Invention

The present invention relates to an apparatus that controls the transport of a chemical stimuli or drug to a particular location. In particular, it relates to an apparatus that accurately controls the concentration of the supply of the chemical stimuli or drug to a location with the concentration of the chemical stimuli or drug being known at each and every point in time through an improved culture chamber wherein the desired concentration is developed.

2. Description of the Prior Art

The maintenance of biological tissue, such as organs isolated from the natural nutrient supply is of great importance. A significant amount of research has been done with regard to organs that have been removed from their natural bodies. The research is quite varied and ranges from simply trying to keep the particular organ alive outside of the body, to studying the complex responses to the isolated organ to various chemical stimuli.

One successful apparatus that administers a chemical stimuli or drug such that its concentration is known at each and every point in time is manufactured under the trademark of ACUSYST 100. The ACUSYST 100 is manufactured by Endotronics, Inc. of Minnesota, which is the assignee of the present invention. The ACUSYST 100 is described in a patent application having Ser. No. 388,136 entitled "Apparatus for Delivering a Controlled Dosage of a Chemical Substance," filed on June 14, 1982. In the ACUSYST 100, the chemical stimuli or drug is delivered into an airtight chamber wherein the volume is kept constant in order to determine the concentration of the chemical stimuli or drug within the chamber. The volume of the chamber is occupied partially by fluid and partially by air. However, due to the gasified nature of the medium in the chamber, further accumulation of gas ocassionally results in the chamber. It has been found that the volume in the chamber fluctuates slightly on ocassion due to temperature and atmospheric pressure fluctuations causing gas accumulation which results in pressure fluctuations. The pressure fluctuations expand and contract the volume of gas within the chamber which distorts the known volume of the medium in the chamber which in turn affects the calculation of the concentration of the chemical stimuli or drug within the chamber.

Although the inaccuracies that may result from a temperature and pressure fluctuation in the chamber are small, constant fluctuations have a cumulative effect in controlling the desired concentration of the chemical stimuli or drug within the chamber.

SUMMARY OF THE INVENTION

The present invention is an improved apparatus that delivers a chemical substance in a controlled manner to a location such that the concentration of the chemical substance affecting the location is controlled at each and every point in time. The apparatus includes a plurality of vessels, each vessel containing a different known concentration of the chemical substance. A valve has a plurality of inlets and a single outlet. Each inlet is fluidly connected to a particular vessel of a different known concentration. An improved culture chamber which maintains a constant volume of the chemical stimuli or drug is used to develop the desired concentration. The chamber is fluidly connected to the outlet of the valve. A first pump is positioned between the valve and the chamber and provides a transport force to deliver the chemical substance to the chamber. A suction tube is positioned within the chamber with an end of the suction tube defining a level of volume desired within the chamber. A second pump is positioned on a downstream location of the suction tube and provides a transport force to remove excess volume within the chamber keeping the volume of the chamber constant.

The valve and the first and second pump are controlled by a computer control system. The computer control system selects a predetermined inlet for fluid connection with the outlet of the valve and then selects a predetermined flow rate, operating the first pump so that a known flow rate with a known concentration is delivered to the chamber. The computer control system controls the operation of the second pump to control the level of the medium within the chamber minimizing fluctuations of the volume within the chamber. In controlling the valve, the first pump and the second pump, the volume is kept constant within the chamber and the concentration of the chemical stimuli or drug is controlled and known at each and every point in time.

BRIEF DESCRIPTION OF THE DRAWINGS

FIG. 3 is a diagrammatical view of the apparatus of the present invention;

DETAILED DESCRIPTION OF THE PREFERRED EMBODIMENT

Figure 1:
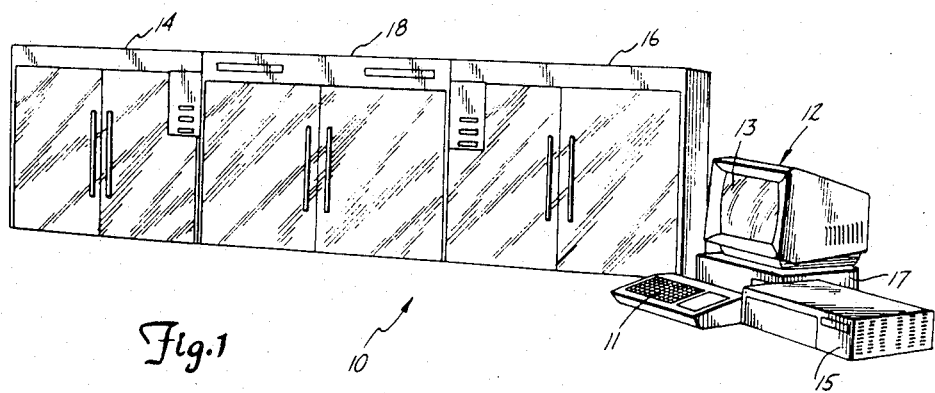
FIG. 1 is a perspective view of the apparatus of the present invention.

The apparatus for administering a controlled patterned delivery of a chemical substance is generally indicated at 10 in FIG. 1. The apparatus is more fully described in an application entitled, "Apparatus for Delivering a Controlled Dosage of a Chemical Substance," filed on June 14, 1982 having Ser. No. 388,136, assigned to the same assignee as the present invention and which is herein incorporated by reference. However, a brief description of the apparatus is included in the present specification for better understanding of the present invention. Throughout the figures, like reference characters will be used to indicate like elements.

The apparatus 10 includes a programmed digital computer control system 12 and a physical plant preferably housed in a plurality of cabinets for treating a biological tissue. The computer control system 12 includes a keyboard and microcomputer unit 11, a CRT display 13, a minidisk unit 15 and an I.O. unit 17. The physical plant preferably contains a left cabinet 14 and a right cabinet 16, the contents of the right cabinet being more fully illustrated in FIG. 2. The left cabinet is the mirror image of the right cabinet and includes the same contents. The contents of the center cabinet 18 positioned between the left and right cabinets is more fully illustrated in FIG. 3.

In one embodiment, the apparatus of the present invention is preferably a perifusion system used to deliver a preselected concentration of a chemical stimuli or drug, such as a nutrient or a hormone in a supportive medium, to a biological cell or tissue in a predetermined controlled manner such that the concentration of the chemical stimuli or drug affecting the cell or tissue is controlled and known at each and every point in time.

Figure 2:
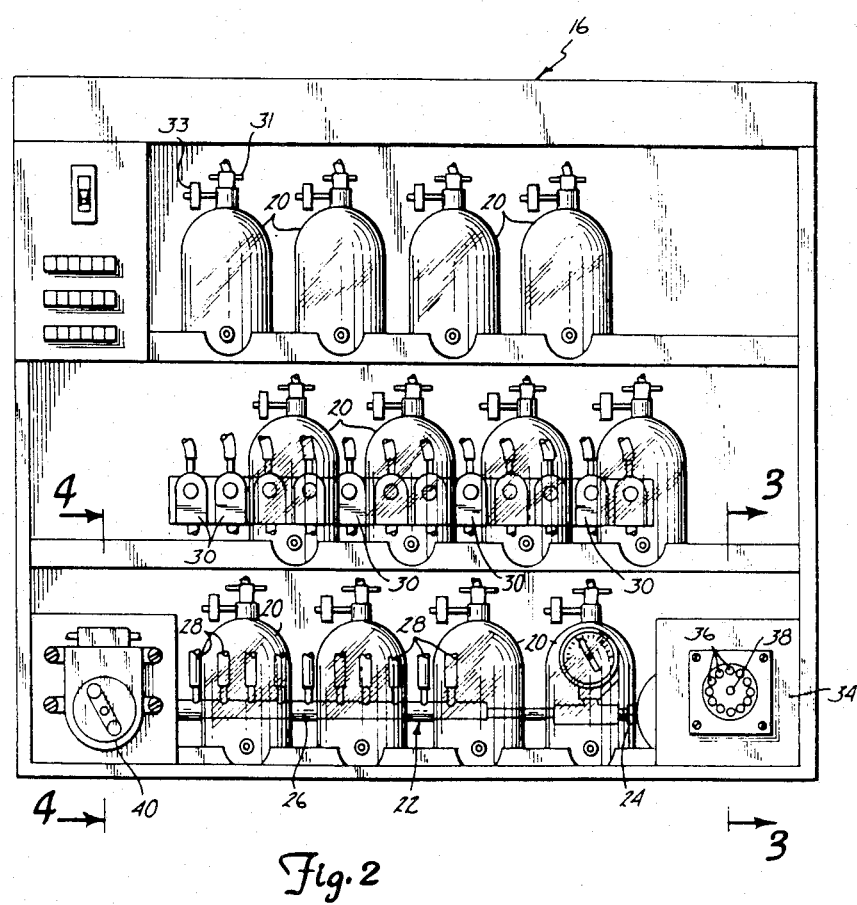
FIG. 2 is a front view of the right cabinet containing vessels, pump and valve.

In FIG. 2, wherein the right cabinet 16 is more fully illustrated, a plurality of flasks 20 hold different concentrations of the particular drug or stimuli in the supportive medium. The particular concentration in each flask 20 is determined prior to any experiment through the computer control system 12.

The concentration of drug or stimuli required in each flask is achieved by mixing the drug or stimuli with the supportive medium. The supportive medium with the drug or stimuli is also equilibrated with $CO_2$ in oxygen. The $CO_2$ in oxygen is delivered to each flask through a gas delivery system generally indicated at 22, as best illustrated in FIG. 3. The gas is metered into the gas delivery system by a pressure regulator mechanism 24. The pressure regulator mechanism maintains a constant predetermined delivery pressure. A manifold 26 distributes the gas into individual gas lines 28 made of suitable conduit. Each line 28 is connected to a corresponding solenoid valve 30. The solenoid valve 30 is connected to the top of each flask 20 by a gas line 29 with a suitable connector. Prior to the connection of the gas line 29 to the flask 20, a sterilizing filter 31 is positioned inline. The gas is introduced into the flask 20 through a gas diffuser such as a fritted glass tube (not shown) that extends into the supportive medium within the flask 20. Each flask 20 has a pressure relief port with a sterile filter 33.

It is desirous to diffuse gas into one or more predetermined flasks 20 at any one time. Diffusion of the gas in one or more flasks 20 is accomplished by opening or closing corresponding solenoid valves 30 under computer control. The regulator 24 maintains the predetermined gas pressure in any line 29 regardless of how many solenoid valves are opened or closed.

Each flask 20 preferably has a lower outlet 32 which is fluidly connected to a corresponding inlet in a valving mechanism 34 by suitable tubing 39. The valving mechanism 34 has a plurality of inlets 36 and a single outlet 38. In one successful embodiment of the present invention, the valve has twelve inlets. The valving mechanism fluidly connects any inlet 36 to the single outlet 38 under the control of computer control system 12. The valve 34 maintains a sterile seal to all lines not connected to outlet 38. All material used for surfaces in contact with the chemical stimuli is chemically inert. Further, the chemical stimuli with supportive medium is maintained within the apparatus in a closed sterile environment.

The outlet 38 of the valving mechanism 34 is connected with tubing 44 to a pumping mechanism 40, preferably a peristaltic pump having a variable flow rate delivery under the control of the computer control system 12. The peristaltic pump 40 provides a transport force for delivering the supportive medium with the chemical stimuli to the tissue. In one successful embodiment, the peristaltic pump has a capability of delivering accurately to within ±0.01 milliliters in any time interval.

Figure 4:
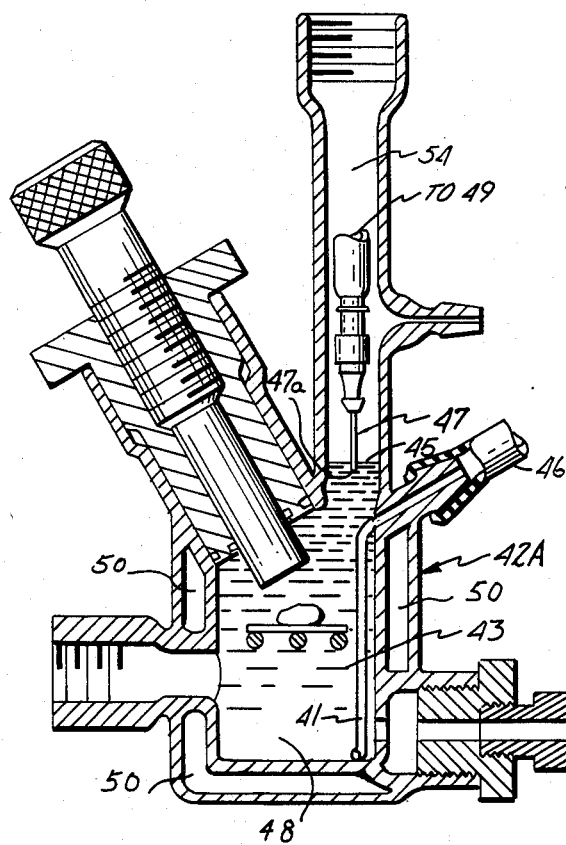
FIG. 4 is a diagrammatical view of the chamber of the present invention.
Figure 6:
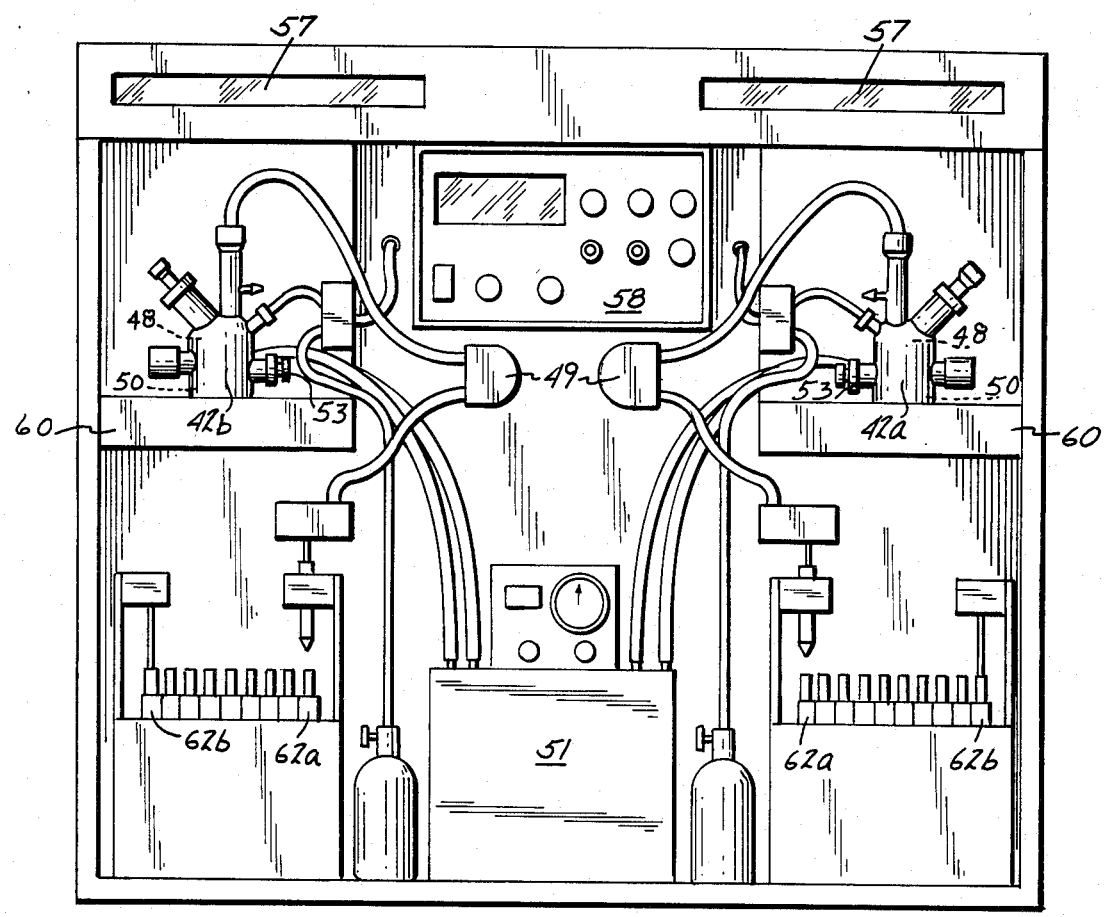
FIG. 6 is a front view of the center cabinet containing the chamber.

The peristaltic pump 40 delivers the drug or chemical stimuli and the supportive medium to an improved culture chamber 42a. The pump 40 is fluidly connected to an inner cavity of the chamber 42a with tubing 46. The tubing 46 is fluidly connected to a tube 41 that delivers the medium proximate the bottom of the chamber 42a, as illustrated in FIG. 4. The pump 40 forces a predetermined amount of the supportive medium into the chamber wherein it is diffused into the medium presently in the chamber, changing the concentration of the medium in the chamber to a new known concentration.

The chamber 42a of the present invention does not have to be kept air tight. Oxygen and carbon dioxide is delivered directly to the chamber 42a from the gas delivery system 22 by suitable conduit 29a controlled by solenoid valve 30a. Silicone tubing (not shown) disposed within the culture chamber permits oxygen and carbon dioxide to pass through the tubing and dissolve into the medium within the chamber without causing bubbles that might affect the volume. The direct delivery of oxygen and carbon dioxide to the chamber 42a permits direct control of oxygen and carbon dioxide without affecting the volume within the chamber.

The medium in the chamber, indicated at 43, is kept at a constant volume. The medium is kept at a constant volume by keeping level 45 of the medium within the chamber 42a at a constant height. The level 45 is kept constant with a suction tube 47 having a lower end 47a. The end 47a is positioned at a predetermined height within the chamber 42a. As the rate of medium being conveyed into the chamber is varied or as the gas pressure in the chamber varies and affects the volume, the suction tube 47 removes excess volume of the medium to keep the level at the predetermined height.

A peristaltic pump 49 controlled by computer control system 12 provides a transport force to remove volume of medium above the end 47a from the chamber 42a. The flow rate of the pump is controlled by the computer control system. The flow rate of pump 49 is at least equal to or greater than the flow rate of pump 40 to maintain a constant volume within the chamber 42a. Preferably, the pump 49 is running constantly during administration of a chemical or drug to the tissue so that a minimum amount of medium per time is removed from the chamber.

The end 47a is preferably positioned at the smallest cross sectional area of the chamber and the pump is controlled by the computer control system 12 to operate at a frequency such that a minimum volume of medium is picked up by the suction tube 47. The end 47a of the suction tube 47 is preferably disposed in a neck portion 54 that includes the upper level 45 of medium within the chamber. The suction tube 47 in one successful embodiment is a 24-gauge blunt-end needle pickup within a neck portion having approximately 0.110 in$^2$ internal cross sectional area picking up approximately one to three microliters of medium in discrete steps from the chamber 42a. The chamber 42a has a volume of approximately 10 milliliters.

Figure 5A:
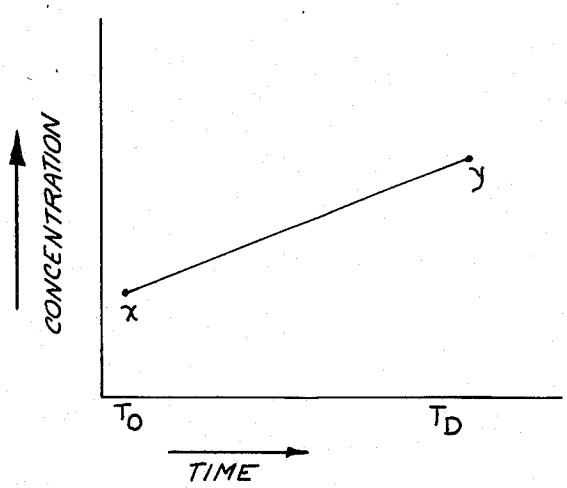
FIGS. 5a and 5b are graphs of time versus concentration illustrating the control of concentration within the chamber.
Figure 5B:
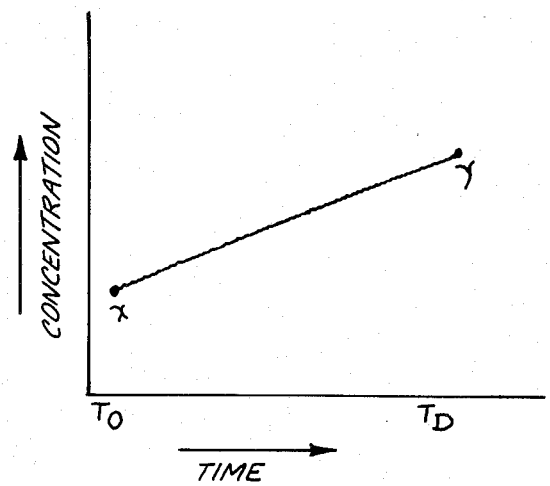

FIGS. 5a and 5b illustrate an example of a concentration change occurring in the chamber 42a from a concentration "x" to a concentration "y". The concentration "x" is the concentration within the chamber 42a at time $T_O$. The concentration "y" is the desired concentration at a desired point in time $T_D$. The rate of concentration change desired is linear between concentrations "x" and "y" over time. It should be understood that the desired rate of change in concentration can also be nonlinear with the following description being applicable to such a nonlinear change. The change occurs according to a relationship of:

$$C(T_D) = C_{HF} + (C_O - C_{HF})e^{-\frac{RT}{V}}$$

wherein:
$C(T_D)$ = Desired concentration in the chamber at time $T_D$.
$C_{HF}$ = Concentration of chemical stimuli or drug and medium being supplied to the chamber from a predetermined holding flask.
$C_O$ = The initial concentration within the chamber at time $T_O$.
R = Rate of supply of the chemical stimuli or drug and medium from the holding flask (ml/hr).
V = Volume of chemical stimuli or drug and medium within chamber (ml).
T = Time (hrs).

The process of changing the concentration is more fully described in an application entitled, "Process for Controlling Patterns of Chemical Stimuli Administration to Biological Tissue," filed on Feb. 19, 1982 and having Ser. No. 350,135, now abandoned assigned to the same assignee as the present invention and which is herein incorporated by reference.

The desired concentration change from concentration "x" to concentration "y" is characterized by a smooth line in FIG. 5a. The actual change in concentration of the chemical stimuli or drug is characterized by a rough line in FIG. 5b. The excess volume is removed in a stepwise manner as the level of the medium and chemical stimuli or drug rises above the end (47a) of the tube (47). The excess volume is removed until the level reaches the end (47a) of the tube. The stepwise removal of excess volume results in a stepwise change in concentration characterized by the rough line in FIG. 5b. The amount of excess volume removed is insignificant to the total volume within the chamber resulting in insignificant concentration deviations from the desired rate of concentration change.

The chamber 42a is a double walled flask having an inner cavity 48 for holding a biological tissue, as illustrated in FIG. 5. The temperature at which the inner chamber 48 is held is controlled by circulating a fluid, such as water or oil, in a jacket 50 between the inner wall of the inner cavity 48 and the outer wall of the flask. The water or oil is circulated from a reservoir bath 51.

The chamber 42a includes side arms 53, 55 for probes to sense temperature and pH with a microprocessor controlled device 57, and analyze for oxygen content in the supportive medium through an oxygen meter 58.

The chamber 42a is positioned on a magnetic stirrer 60 for proper diffusion of the incoming concentration of chemical stimuli in the supportive medium within the chamber 42a. Preferably, the stirrer is operable at slow speeds and is capable of long duty cycles. In addition, the stirrer is of a type that minimizes heat transfer to the chamber.

In the embodiment illustrated in FIG. 3, the chamber 42a contains a cell or cells and is operated as a perifusion system. The cell responds to the change and rate of change of concentration by secreting a substance which diffuses into the medium.

From the chamber 42a, excess supportive medium is transported to a fraction collector 62a by pump 49. The fraction collector 62a includes a plurality of test tubes wherein the supportive medium is dropped into a predetermined test tube. The pump 49 also maintains the culture chamber 42a in a sterile environment and eliminates the need for a sterile filter after the culture chamber. In addition, the pump 49 eliminates the dead time involved in moving fluid to the fraction collector that resulted in prior art airtight culture chambers.

The supportive medium is removed from the test tube automatically or manually to an analyzer 66. The results provided by the analyzer 66 are recorded by the computer control system 12.

As will be noted from FIG. 3, the central cabinet 18 has a second chamber 42b and a second fraction collector 62b. The central cabinet 18 is divided substantially into two halves with one being the mirror image of another each half preferably sharing the same reservoir bath 52. Concentrations of the drug or stimuli are delivered from left cabinet 14 to the chamber 42b. As is typical in a perifusion system, either the right or left cabinet is used to run the actual experiment and the other cabinet is used to run a control.

The change in concentration of the substance within the culture chamber in response to a known supply substance concentration being delivered to the culture chamber with a known volume at a known rate can be readily determined by use of the system in conjunction with a digital computer.

In the present process a certain rate dependent volume was removed from the culture chamber during a known time interval. Simultaneously, a drop of another rate dependent volume is being formed at the top of the culture chamber. Eventually, this drop enters the culture chamber and equilibrates with the substance in the culture chamber.

To initiate the simulation sequence, the following parameters were defined:
Culture Chamber Volume (V)—ml
Culture Chamber Starting Concentration ($C_i$)—units/ml
Supply Drug Starting Concentration in Holding Flasks ($C_s$)—units/ml
Rate of Fluid Delivery (R)—ml/hr
Integration Interval (t)—seconds With these parameters defined, the following loops were programmed in the digital computer to simulate the process. The following jobs were performed during each loop for each chemical stimuli:

1. The total number of units ($U_t$) in the culture chamber was determined ($U_t = C_i$ units/ml × V ml).
2. A volume ($V_R$) was removed from the culture chamber. $V_R$ is a function of R and t $$\left( V_R = \frac{R \text{ ml/hr} \times t \text{ sec}}{3600 \text{ hr/sec}} \right).$$

3. The new volume of the culture chamber was determined ($V = V - V_R$).
4. The amount of units removed ($U_R$) from the culture chamber with $V_R$ was determined. $U_R$ is a function of $C_i$ and $V_R$ ($U_R = (C_i \text{ units/ml}) (V_R \text{ ml})$).

5. The new $U_t$ in the culture chamber was determined $(U_t = U_t - U_R)$.
6. A volume was added to the culture chamber ($V_A$) from the holding flask. If the culture chamber was airtight, $V_A$ would be equivalent to $V_R$ ($V_A = V_R$).
7. The new volume of the culture chamber was determined $(V = V + V_A)$.
8. The amount of units added to the culture chamber ($U_A$) with $V_A$ was determined ($U_A = (C_s$ units/ml) ($V_A$ ml))
9. The new $U_t$ in the culture chamber was determined $(U_t = U_t + U_A)$.
10. The new $C_i$ was determined $$\left( C_i = \frac{U \text{ units}}{V \text{ ml}} \right)$$

When the culture chamber volume is kept constant, the concentration of any diffusable substance can be determined mathematically (equation (1)). This equation is derived from the computer-aided analysis of the process.

$$(C_{(t)} = C_s + (C_i - C_s)e^{-(Rt)/V}). \tag{1}$$

$C_{(t)}$ = concentration in culture chamber at time t
$C_s$ = concentration of chemical stimulus in holding flask (final culture chamber concentration at $t = \infty$)
$C_i$ = initial culture chamber concentration (t=0)
R = rate of supply substance delivery from holding flask to culture chamber (ml/hr)
V = volume of media in culture chamber (ml)
t = time (hrs)

To test the ability of equation (1) to accurately predict the concentration of the substance in the culture chamber when either a higher or lower concentration of the same drug was being delivered to the culture chamber at a constant rate, the following experiments were conducted. A dye, methyl orange (MO), was selected as the supply substance in these experiments because: (1) the concentration of the dye in the culture chamber could be assayed by measuring percent transmission at a maximum absorbance of 460 nanometers utilizing a spectrophotometer, and (2) at the completion of the assay, the sample of culture chamber fluid could be placed back into the culture chamber. This is important because it allowed continuous sampling over time without altering any of the parameters in equation (1) (i.e., culture chamber volume and $C_i$).

To test the ability of equation (1) to predict changes in culture chamber concentration when a higher concentration of the same drug was delivered at a constant rate from the holding flask, 100 ml of a standardized solution was placed in the holding flask. This solution of MO was adjusted so that it produced a reading of 10% transmission and was considered to be a 100% concentrated solution. 20 ml of distilled water (100% transmission) was placed in the culture chamber and was considered a 0% concentrated solution. The values between 10 and 100 percent transmission lie on the linear portion of a standard curve with a correlation coefficient of 0.99995 comparing known concentrations of MO and percent transmission. The 100% solution was pumped into the culture chamber at a rate of 18.5 ml/hr. At 15 minute intervals over a period of two hours, the pump was turned off and a 2 ml sample from the culture chamber was removed and assayed with a photospectrometer. The percent transmission was converted to optical density and the concentration recorded from the standard curve. The sample was then replaced in the culture chamber and the pump restarted.

To test the ability of equation (1) to predict changes in culture chamber concentration when a lower concentration of the supply drug was delivered from the holding flask, 100 ml of distilled water (0% concentration) was placed in the holding flask. 20 ml of a 100% concentrated solution of MO was placed in the culture chamber. The 0% concentrated solution was then pumped into the culture chamber and the methyl orange concentration determined as described above. The results indicated that equation (1) can be used as an expression to describe the present process.

With the capability of being able to accurately predict concentration changes in the culture chamber, it is now possible to emulate any data where a diffusable substance concentration is plotted as a function of time, in the culture chamber. With the initial concentration of the substance in the culture chamber known and the value of the desired final concentration in the culture chamber over a known time interval also known ($C_{s \cdot t}$). The concentration of the substance to be placed in the holding flask can be determined by a manipulation of equation (1) to derive equation (6).

$$c_{(t)} = C_s + (C_i - C_s)e^{-(Rt)/V} \tag{1}$$

since $C_{s \cdot t} = C_{(t)}$, substituting $$C_{s \cdot t} = C_s + (C_i - C_s)e^{-(Rt)/V} \tag{2}$$

factoring:

$$C_{s \cdot t} = C_s + C_i e^{-(Rt)/V} - C_s e^{-(Rt)/V} \tag{3}$$

subtracting $C_i e^{-(Rt)/V}$ from each side:

$$C_{s \cdot t} - C_i e^{-(Rt)/V} = C_s - C_s e^{-(Rt)/V} \tag{4}$$

factoring:

$$C_{s \cdot t} - C_i e^{-(Rt)/V} = C_s(1-e)^{-(Rt)/V} \tag{5}$$

solving for $C_s$:

$$C_s = \frac{C_{s \cdot t} - C_i e^{-\frac{Rt}{V}}}{1 - e^{-\frac{Rt}{V}}} \tag{6}$$

Figure 7:
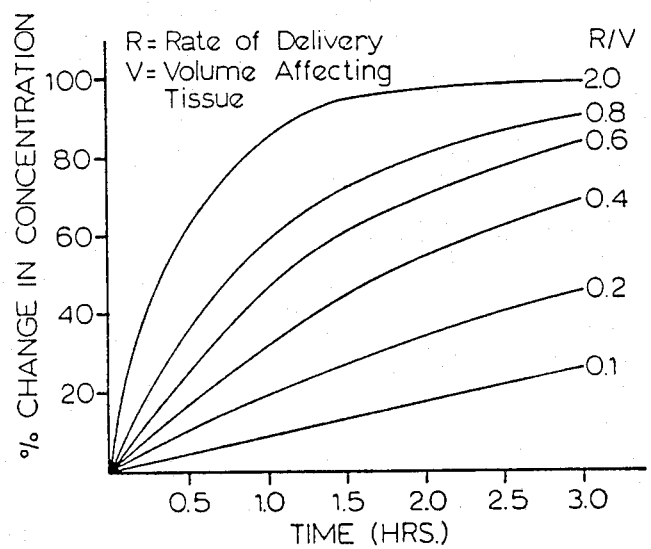
FIG. 7 is a graph illustrating a plurality of possible R/V ratios.

To more precisely emulate in-vivo conditions, a desired rate of delivery (R) and a desired volume (V) affecting the tissue in the culture chamber must be determined. In other words, if it is desirous to change the concentration of the substance within the culture chamber from the initial concentration ($C_i$) to a different concentration ($C_{(t)}$) linearly with respect to time, the change from $C_i$ to $C_{(t)}$ is a function of R and V. As shown graphically in FIG. 7, a ratio of R/V affects the maximum percent change that can occur over a known time interval. The maximum percent change that is possible during a known time interval varies directly with the R/V ratio. However, the linearity of the line between the initial point ($C_i$) and the final point ($C_{(t)}$) over a known time interval varies inversely to the R/V ratio.

If a large linear increase in concentration in the culture chamber is desired during a given time interval, the slope of a line from $C_i$ to $C_{(t)}$ is also great. Since the linearity of the increase in concentration in the culture chamber is an inverse function of the R/V ratio, large increases pose problems in reaching the point $C_{(t)}$ in a given time interval in a linear fashion. The linearity of the change in concentration can be preserved by increasing the concentration of the substance being supplied, thus not affecting the R/V ratio.

This is not the case if a large decrease in concentration in the culture chamber is desired, as the minimum concentration of a substance in a holding flask can be zero. Thus, the minimum R/V ratio (maximum linearity) must be determined. This R/V ratio is then compared with FIG. 10. To determine if the calculated R/V ratio will emulate the desired degree of linearity between the data points ($C_i$ and $C_{(t)}$) in question.

To determine the minimum R/V ratio required to achieve the percent concentration change between $C_i$ and $C_{(t)}$, the negative slope for the decreasing concentration is analyzed over a known desired time interval wherein the supply substance concentration ($C_s$) equals zero. The amount of change ($\Delta_c$) between $C_i$ and $C_{(t)}$ over the time interval t is determined by equation (7):

$$c = \frac{C_i - C_{(t)}}{C_i} \qquad (7)$$

A 100% change would occur if $C_{(t)}$ was zero ($\Delta_c = 1$). Thus, the concentration at $C_{(t)}$ would be the difference between a 100% change ($\Delta_c = 1$) and the actual change, as expressed by equation (8):

$$C_{(t)} = 1 - \Delta_c \qquad (8)$$

To drive to a 100% change the supply substance concentration ($C_s$) must be zero. If the initial concentration ($C_i$) is assumed to be one, equation (8) can be substituted in equation (3), the determination of which is discussed subsequently, with $C_s = 0$ and $C_i = 1$ and an expression for the minimum R/V ratio derived:

$$C_{(t)} = C_s + (C_i - C_s)e^{-(Rt)/V} \qquad (9)$$

substituting equation (2) into (3) to obtain equation (4):

$$1 - \Delta_c = 9 + (1-0)e^{-(Rt)/V} \qquad (10)$$

simplifying:

$$1 - \Delta_c = e^{-(Rt)/V} \qquad (11)$$

simplifying:

$$\ln(1 - \Delta_c) = -(Rt)/V \qquad (12)$$

solving for R/V:

$$R/V = -1/t \ln(1 - \Delta_c) \qquad (13)$$

substituting equation (7) into equation (13):

$$\frac{R}{V} = \frac{-1}{t} \ln\left(1 - \frac{C_i - C_{(t)}}{C_i}\right) \qquad (14)$$

simplifying:

$$\frac{R}{V} = \frac{-1}{t} \ln\left(\frac{C_{(t)}}{C_i}\right) \qquad (15)$$

Equation (15) provides an expression for the minimum R/V ratio required to drive to a desired concentration in a given time interval in the culture chamber. If the linearity provided by the calculated R/V ratio is not adequate to emulate a given set of data, the change in concentration can be broken into at least two steps. Assuming we wish to emulate a set of data that changes linearly from an initial concentration of $C_i$ to a final concentration of $C_{(t)}$ in a time interval of t, the first step is to break this change into two intervals. This is accomplished by setting a new point (A) at a point half way between $C_i$ and $C_{(t)}$ (i.e., at $t = \frac{1}{2} t$). Thus, secondly, a new $C_s$ in the holding flask and a new minimum R/V ratio can be calculated using $C_i$ as the initial point and changing point A to a new $C_{(t)}$ for a final point. Since the percent change required between $C_i$ and A is less than between $C_i$ and the original $C_{(t)}$, the minimum R/V will be lower and the linearity increased. This procedure can be repeated until a satisfactory linearity is achieved. In this manner, the process of the present invention emulates in-vivo conditions and other conditions and provides a method of knowing the concentration affecting the tissue at each and every point in time.

In practice, the supply substance concentration is changed using a preferred method wherein a plurality of holding flasks is used with each flask containing a different concentration ($C_s$) of the supply substance. When a different concentration of the supply drug is needed, a change is made from one holding flask to another. It will be understood by those skilled in the art that the number of flasks needed and the differences between the concentrations of the supply drug in the flasks will be a function of the particular application of the process.

Peristaltic pumps are a preferred apparatus for conveying the supply substance from the holding flasks to the culture chamber. The rate of delivery is controlled by a suitable variable speed motor and controller which drive the pump.

The known amounts removed from the culture chamber are then assayed to determine the response of the tissue to the substance. In addition, the culture chamber may be designed to accept probes, which are attached to suitable instrumentation, for monitoring pH, oxygen consumption, temperature, selective ions, membrane potentials and other variables of interest.

With the responses of the tissue known as a function of time and with the concentrations of the substance affecting the tissue also known as a function of time, relationships are established as to cause and effect, through known mathematical methods. With the immediately above-described procedure repeated and performed against "control" specimens, proper drug concentration and administration to a particular tissue are determined.

As will be appreciated by those skilled in the art, the present process is applicable to the delivery of more than one chemical stimuli at a time to the culture chamber by mixing the substances together in the same holding flask. In the case of multiple substances being utilized, the minimum R/V ratio must be determined from the greatest slope in each time interval. This result will be the same for all changes in that interval. Complex experiments, heretofore not possible, may be carried out in-vitro emulating known in-vivo and other conditions by use of the present invention. In-vitro conditions are adjustable at will and the responses observable without costly live animal experimentation. In addition, unwanted interference from bodily responses to experimentation directed at the particular tissue is eliminated thereby reducing the number of experiments needed to achieve statistical reliability.

Once the relationships between chemical stimuli and tissue are determined, the process is used to deliver the chemical stimuli to subsequent tissue in an optimal manner. For example, organ transplants are kept biologically alive longer using the process to deliver nutrients at a rate and concentration as the transplant needs the nutrients.

Another important advantage of the process of the present invention is that it is particularly well suited for control by electronic means such as a programmed digital computer together with appropriate interface circuitry. More specifically, the administration of the rate of delivery and the concentrations of the chemical stimuli supplied to the tissue are controllable by a suitable microprocessor-based control system. Once programmed with the desired changes in concentration with respect to time, the microprocessor manipulates the process apparatus, such as the peristaltic pump. If a plurality of flasks are used to hold different concentrations of the chemical stimuli, then the switching from flask to flask is controlled through the microprocessor.

Although the present invention has been described with reference to preferred embodiments, workers skilled in the art will recognize that changes may be made in form and detail without departing from the spirit and scope of the invention.

What is claimed is:

1. An apparatus for delivering a controlled dosage of a chemical substance to a chamber containing cells or tissue, the apparatus comprising:

a plurality of vessels, each vessel containing a different known concentration of the chemical substance;

valving means having a plurality of inlets and a single outlet for fluidly connecting a preselected inlet to the single outlet;

first conduit means for fluidly connecting the vessels to the inlets;

a culture chamber for receiving the chemical substance having a lower fluid chamber and an upper neck portion, the neck portion being of smaller diameter than the fluid chamber and the chemical substance having an upper level in the neck portion, the neck portion communicating with the fluid chamber and the culture chamber further including an inlet and a second conduit means having a lower end disposed within the neck portion defining a predetermined level of the chemical substance in the culture chamber;

third conduit means for fluidly connecting the single outlet of the valving means to the inlet of the culture chamber;

first pump means fluidly connected to the third conduit means for providing a transport force to the chemical substance in a flow controlled manner for delivering the chemical substance to the culture chamber;

second pump means fluidly connected to the second conduit means for removing excess volume of the chemical substance from the culture chamber and keeping the volume within the culture chamber constant; and control means for controlling the valving means having means for providing input signals and means for providing signals indicative of a desired program of administation such that a preselected inlet is fluidly connected to the outlet for presenting a preselected known concentration of the chemical substance to the chamber, and for controlling the first pump means for providing a transport force to the chemical substance, and for controlling the second pump means so that the volume in the chamber is kept constant, and including means for controlling the concentration of the chemical substance in the chamber according to the program of administration corresponding to the equation $$C_{(t)} = C_s + (C_i - C_s)e^{-(Rt)/V}$$

wherein
t = integration time interval
V = volume of fluid within the culture chamber affecting the cells or tissue in which the chemical substance is being delivered
R = the rate of delivery of the chemical substance to the culture chamber
$C_i$ = the initial concentration level of the chemical substance in the integration time interval within the culture chamber
$C_{(t)}$ = the final concentration of the chemical substance in the integration time interval within the culture chamber
$C_s$ = the concentration of the chemical substance being delivered in the integration time interval from the vessels into the culture chamber,
wherein the means for controlling the concentration selects values of R/V and $C_s$ such that the concentration change between $C_i$ and $C_{(t)}$ is linear.

2. The apparatus of claim 1 wherein the control means includes a programmed digital computer system.

3. The apparatus of claim 1 wherein the first pump means is a peristaltic pump.

4. The apparatus of claim 1 wherein the second pump means is a peristaltic pump.

5. The apparatus of claim 1 wherein the third conduit means is a needle pickup.

6. An apparatus comprising:

a plurality of different source concentrations of a chemical substance;

valving means having a plurality of inlets and a single outlet for fluidly connecting a preselected inlet to the single outlet;

first conduit means for fluidly connecting the source concentrations to the inlets;

a chamber for receiving the chemical substance in a controlled manner and environment having a lower fluid chamber and an upper neck portion, the neck portion having a smaller diameter than the fluid chamber and the chemical substance having an upper level in the neck portion;

second conduit means for fluidly connecting the single outlet of the valving means to the chamber;

third conduit means having a lower end disposed within the neck portion defining a predetermined level of the chemical substance within the chamber;

first pump means fluidly connected to the second conduit means for providing a transport force to the chemical substance in a flow controlled manner for delivering the chemical substance to the chamber;

second pump means fluidly connected to the third conduit means for removing excess volume of the chemical substance from the chamber keeping the level within the chamber constant; and control means for controlling the valving means having means for providing input signals and means for providing signals indicative of a desired program of administration such that a preselected inlet is fluidly connected to the outlet for presenting a preselected known concentration of the chemical substance to the chamber, and for controlling the first pump means, and for controlling the second pump means so that the volume within the chamber is kept constant, and including means for controlling the concentration of the chemical substance being delivered to the chamber according to the program of administration corresponding to the equation $$C_{(t)} = C_s + (C_i - C_s)e^{-(Rt)/V}$$

wherein t = the integration time interval

V = volume of fluid within the chamber in which the chemical substance is being delivered R = the rate of delivery of the chemical substance to the chamber $C_i$ = the initial concentration level of the chemical substance in the integration time interval within the chamber $C_{(t)}$ = the final concentration of the chemical substance in the integration time interval within the chamber $C_s$ = the concentration of the chemical substance being delivered in the integration time interval from the source concentrations into the chamber, wherein the means for controlling the concentration selects values of R/V and $C_s$ such that the concentration changes between $C_i$ and $C_{(t)}$ is linear.

7. The apparatus of claim 6 wherein the control means includes a computer control system.

* * * * *